United States Patent
Parashar et al.

(10) Patent No.: US 9,360,536 B2
(45) Date of Patent: *Jun. 7, 2016

(54) DEVICES AND METHODS USING SWIPE DETECTION

(71) Applicant: Coin, Inc., San Francisco, CA (US)

(72) Inventors: Kanishk Parashar, San Francisco, CA (US); Karthik Balakrishnan, Palo Alto, CA (US); Bret Foreman, San Francisco, CA (US); Rory Nordeen, San Francisco, CA (US)

(73) Assignee: Coin, Inc., San Francisco, CA (US)

( * ) Notice: Subject to any disclaimer, the term of this patent is extended or adjusted under 35 U.S.C. 154(b) by 18 days.

This patent is subject to a terminal disclaimer.

(21) Appl. No.: 14/665,747

(22) Filed: Mar. 23, 2015

(65) Prior Publication Data

US 2015/0192647 A1    Jul. 9, 2015

Related U.S. Application Data

(63) Continuation of application No. 14/257,730, filed on Apr. 21, 2014, now Pat. No. 9,010,651, which is a continuation of application No. 13/974,524, filed on Sep. 24, 2013, now abandoned.

(51) Int. Cl.
| | |
|---|---|
| *G06K 19/06* | (2006.01) |
| *G01R 33/06* | (2006.01) |
| *G01R 27/26* | (2006.01) |
| *G01R 33/07* | (2006.01) |

(52) U.S. Cl.
CPC .......... *G01R 33/06* (2013.01); *G01R 27/2605* (2013.01); *G01R 33/072* (2013.01); *G06K 19/06206* (2013.01)

(58) Field of Classification Search
CPC .................... G06K 19/06206; G06K 19/12
USPC .......................... 235/287, 482, 493
See application file for complete search history.

(56) References Cited

U.S. PATENT DOCUMENTS

| | | | | |
|---|---|---|---|---|
| 7,784,687 | B2 * | 8/2010 | Mullen et al. | 235/380 |
| 7,954,724 | B2 * | 6/2011 | Poidomani et al. | 235/492 |
| 9,010,651 | B2 * | 4/2015 | Parashar et al. | 235/492 |
| 2004/0035942 | A1 * | 2/2004 | Silverman | 235/493 |

OTHER PUBLICATIONS

Office Action for U.S. Appl. No. 13/974,524, dated Jun. 27, 2014, 12 pages.
Office Action for U.S. Appl. No. 14/257,730, dated Jun. 26, 2014, 12 pages.
Office Action for U.S. Appl. No. 14/257,730, dated Dec. 4, 2014, 13 pages.
Notice of Allowance for U.S. Appl. No. 14/257,730, dated Jan. 23, 2015, 13 pages.

\* cited by examiner

*Primary Examiner* — Daniel St Cyr
(74) *Attorney, Agent, or Firm* — Amin, Turocy & Watson, LLP

(57) ABSTRACT

The present invention relates devices and methods using swipe detection. A swipeable computer of the present invention comprises a capacitive detector having an output, a switchable magnetic field sensor having an output, a memory unit, and a logic unit. The memory unit stores a standard capacitance change and a standard magnetic field change. The logic unit is electrically connected to the capacitive detector output, the switchable magnetic field sensor, the switchable magnetic field sensor output, and the memory unit. The logic unit of the swipeable computer is adapted to determine if the capacitive detector output corresponds to the standard capacitance change, to enable the switchable magnetic field sensor if the change in capacitance corresponds to the standard capacitance change, and to determine if the switchable magnetic field sensor output corresponds to the standard magnetic field change.

15 Claims, 5 Drawing Sheets

DEVICES AND METHODS USING SWIPE DETECTION

CROSS-REFERENCE TO RELATED APPLICATIONS

This application is a continuation of U.S. patent application Ser. No. 14/257,730 filed Apr. 21, 2014, and entitled "DEVICES AND METHODS USING SWIPE DETECTION," the entirety of which is incorporated herein by reference, which is a continuation of U.S. patent application Ser. No. 13/974,524 filed Sep. 24, 2013, and entitled "DEVICES AND METHODS USING SWIPE DETECTION," the entirety of which is incorporated herein by reference.

BACKGROUND OF THE INVENTION

The present invention relates to cards using magnetic stripes, such as credit cards and debit cards, and more particularly, to devices and methods for swipe detection for use with swipeable computers having dynamic magnetic stripes.

Magnetic stripe cards have been in use since the 1960s. Since that time, the formats for storing and reading information on magnetic stripe cards have been standardized and the technology has been widely adopted. Some of the standards covering magnetic stripe cards include International Organization for Standardization (ISO) standards, ISO-4909, ISO-7810, ISO-7811, ISO-7812, ISO-7813, and ISO-8583. Based on these standards, millions of readers for magnetic stripe cards have been installed at merchants, points of service, and other locations worldwide.

To improve the functionality of magnetic stripe cards and still take advantage of the installed base of card readers, cards using dynamic magnetic stripes have emerged. These dynamic magnetic stripe cards function with the currently installed base of magnetic card readers and have several advantages including the ability to store and transmit information from multiple magnetic cards as well as the possibility for improved security.

Dynamic stripes must produce a time-varying magnetic field that duplicates the field produced by a non-dynamic stripe passing by the read-head. Creating this field requires energy and precise timing of the field variations. The process of detecting that a card user is swiping a dynamic card in a reader, along with the process of controlling the exact timing of the magnetic variations is collectively called "swipe sense."

The quality of the swipe sense is determined by three metrics: 1) the frequency of "false alarms," where the swipe sense falsely signals that a swipe is happening; 2) the accuracy of the timing (relative to read head position) of the signal from the swipe sense electronics; and 3) the average continuous power required by the swipe sense electronics.

Because dynamic magnetic cards are often designed at or near the dimensions of a standard credit card, they have limited space for a battery or other power source. The present invention relates to devices and methods for swipe detection that are used to reduce the power consumption associated with swipe detection in these devices without substantial degradation in the frequency of false alarms and timing accuracy.

SUMMARY OF THE INVENTION

The present invention relates to devices and methods for swipe detection that are used to reduce the power consumption associated with swipe detection without substantial degradation in the frequency of false alarms and timing accuracy.

A swipeable computer of the present invention comprises a capacitive detector having an output, a switchable magnetic field sensor having an output, a memory unit storing a standard capacitance change and a standard magnetic field change. The swipeable computer also includes a logic unit electrically connected to the capacitive detector output, the switchable magnetic field sensor, the switchable magnetic field sensor output, and the memory unit. The logic unit of the swipeable computer is adapted to determine if the capacitive detector output corresponds to the standard capacitance change, to enable the switchable magnetic field sensor if the change in capacitance corresponds to the standard capacitance change, and to determine if the switchable magnetic field sensor output corresponds to the standard magnetic field change.

A method for detecting a swipe of a swipeable computer includes sensing a change in capacitance and determining if the change in capacitance corresponds to a standard capacitance change. If the change in capacitance does not correspond to a standard capacitance change, the magnetic field sensor remains off. The method also includes enabling a magnetic field sensor if the change in capacitance corresponds to the standard capacitance change. After the magnetic field sensor is enabled, the method includes sensing a magnetic field change. Next, the method includes determining if the magnetic field change corresponds to a standard magnetic field change.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

Figure 1:
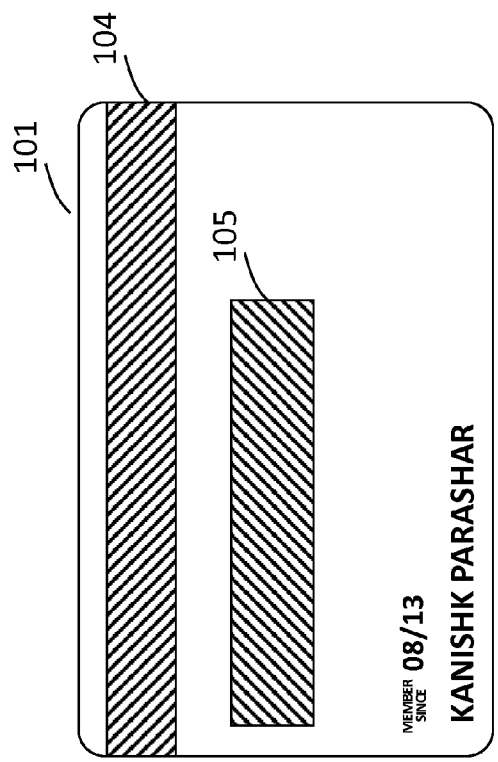
FIG. 1 illustrates a front and back view of an exemplary embodiment of the swipeable computer of the present invention.
Figure 1:
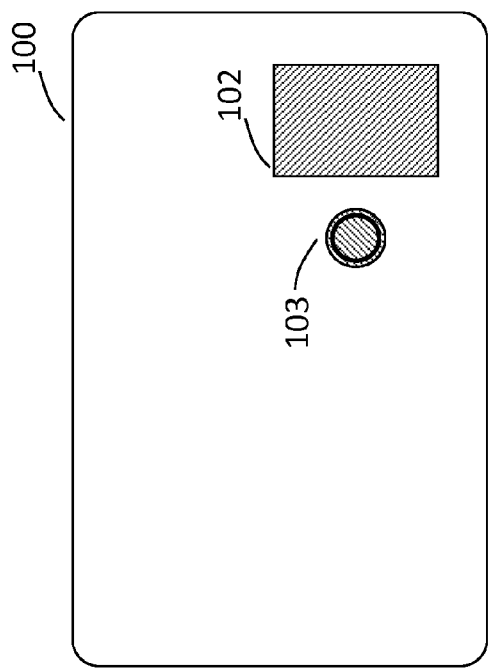

FIG. 1 illustrates a front 100 and back 101 view of an exemplary embodiment of the swipeable computer of the present invention. As seen from the front view 100, the swipeable computer may include a display 102 and a button 103. The display 102 may be an electronic ink (e-ink), LCD, or other type of display. The display 102 is optimally a low-power display. The button 103 may be a mechanical contact button, a capacitive button, or other similar button. The swipeable computer of the present invention may have approximately the same dimensions as a traditional credit card or it may have other dimensions depending on the desired application.

As seen from the back view 101, the swipeable computer may include a dynamic stripe area 104 and a signature area 105. The signature area 105 may be an area, similar to those in standard financial cards, for user authorization of the swipeable computer.

Figure 2:
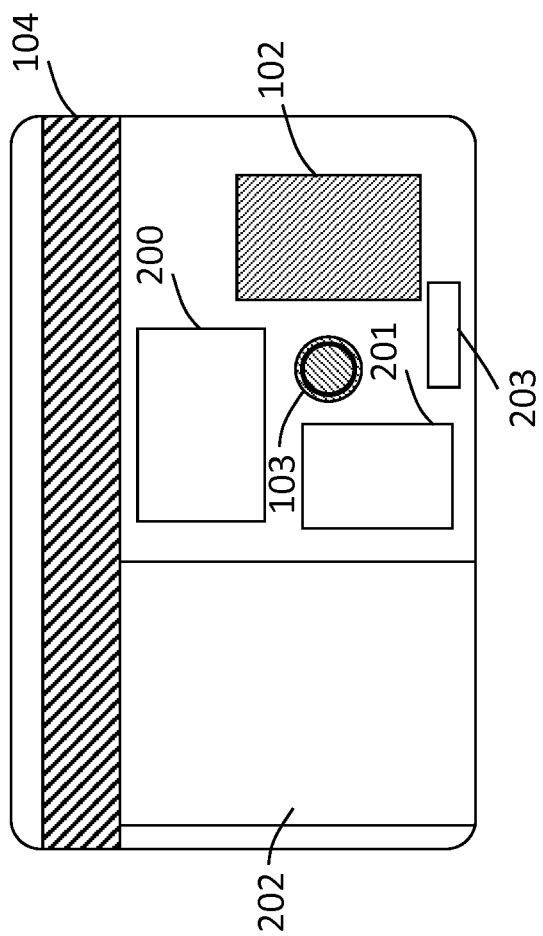
FIG. 2 illustrates a partial cut-away view of an exemplary embodiment of the swipeable computer of the present invention showing certain components of the swipeable computer.

FIG. 2 illustrates a partial cut-away view of an exemplary embodiment of the swipeable computer of the present invention. The figure illustrates an exemplary arrangement of the display 102, button 103, and dynamic stripe area 104 of FIG. 1 in the swipeable computer. In addition, FIG. 2 also shows that the swipeable computer may contain a wireless communication unit 200, a logic unit 201, a power source 202, and a memory unit 203. The arrangement of the components in FIG. 2 is merely exemplary, and the components may be arranged differently according to design needs.

The wireless communication unit 200 may use radio frequency such as Bluetooth, near field communication (NFC), or Wi-Fi, or the wireless unit 200 may use infrared or another transmission protocol. The logic unit 201 may be a processor, a programmable logic array, hardwired logic, or another similar logic device. While the logic unit 201 is depicted in FIG. 2 as a single device, the logic unit of the present invention may comprise multiple devices and may be incorporated in other components of the swipeable computer. The power source 202 is a battery, micro fuel cell, or the like.

Figure 3:
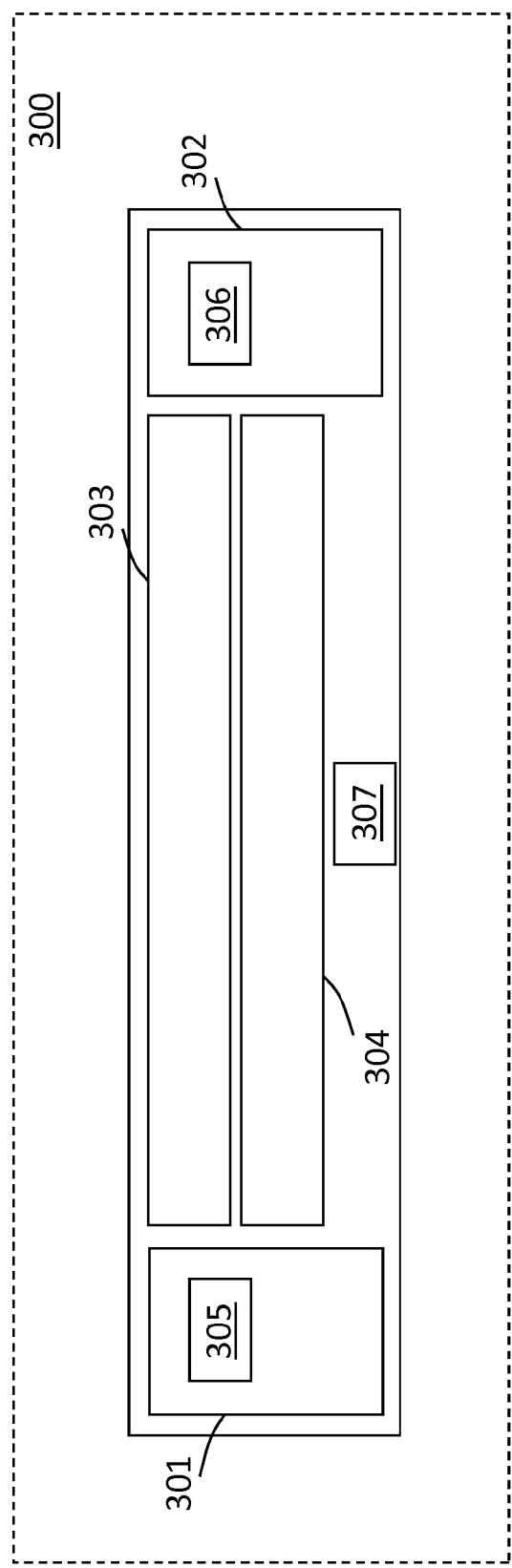
FIG. 3 illustrates an embodiment of the dynamic stripe of the swipeable computer of the present invention.

FIG. 3 illustrates an embodiment of the dynamic stripe 300 of the swipeable computer of the present invention. As show in the figure, the dynamic stripe 300 comprises a plurality of swipe detectors 301, 302 and one or more dynamic magnetic emulators 303, 304. The dynamic magnetic emulators 303, 304 comprise coils that create time-varying magnetic fields to communicate data to a magnetic card reader.

In the present invention, the swipe detectors 301, 302 each comprise a capacitive detector 305, 306. The capacitive detectors 305, 306 may be located near the edges of the swipeable computer to better detect the initiation of a swipe in a magnetic card reader. The swipe detectors 301, 302 may include one or more switchable magnetic field sensors 307, 308. The magnetic sensing for the magnetic field sensors 307, 308 may be integrated into or use one or more of the coils.

Embodiments of the present invention may include the components shown in the attached figures and described above. Accordingly, in one embodiment, the swipeable computer of the present invention comprises a display 102, a button 103, a wireless communication unit 200, a power source 202, a dynamic magnetic emulator 303, 304, a capacitive detector 305, 306, a switchable magnetic field sensor 307, 308, a memory unit 203, and a logic unit 201. In another embodiment of the present invention, an apparatus for detecting a swipe of a swipeable computer in a magnetic card reader comprises a capacitive detector 305, 306, a switchable magnetic field sensor 307, 308, a memory unit 203, and a logic unit 201.

Each capacitive detector 305, 306 is sensitive to changes in capacitance due to changes in the materials proximate to the swipeable computer. Thus, each capacitive detector 305, 306 is sensitive to a change in capacitance as the swipeable computer moves from open air into proximity of the materials of which magnetic card readers are made. The capacitive detectors 305, 306 may comprise a standard capacitive sensor or a sensor specially designed and/or fabricated to sense a change in capacitance associated with initiation of a swipe in a magnetic card reader. The capacitive sensor may be specially designed and/or fabricated by selecting dimensions and/or materials for the sensor that increase the relative change in capacitance sensed between the open air and the proximity of the magnetic card reader. Each capacitive detector 305, 306 has an output, the value of which corresponds to the change in capacitance that the capacitive detectors 305, 306 detect.

Each capacitive detector 305, 306 of the present invention may always be on such that it constantly detects changes in capacitance or it may be switched by the button of the swipeable computer, by an integrated motion sensor, or by some other means.

The logic unit 201 is electrically connected to the output of each capacitive detector 305, 306 and determines if the output corresponds to a standard capacitance change. The standard capacitance change is a value, a range, a signal, a waveform, or the like that corresponds to the expected change in capacitance caused by initiating a swipe of the swipeable computer in a magnetic card reader. The standard capacitance change may be determined by recording and combining the output of one or more of the capacitive detectors 305, 306 in one or more swipeable computers of the present invention resulting from swiping the swipeable computers in one or more standard card readers.

The standard capacitance change is stored in a memory unit 203 in the swipeable computer. The memory unit 203 may be a single device or multiple devices and may be incorporated in other components in the swipeable computer. The logic unit 201 compares the capacitive detector 305, 306 output to the standard capacitance change through analog or digital means or a combination of the two. If the logic 201 unit determines that that the capacitive detector 305, 306 output corresponds to the standard capacitance change, then the logic unit 201 enables the switchable magnetic field sensor 307, 308 for a period of time.

To conserve power, the switchable magnetic field sensor 307, 308 defaults to inactive. But, as described above, the logic unit 201 enables the switchable magnetic field sensor 307, 308 if it determines that that the capacitive detector 305, 306 output corresponds to the standard capacitance change. Once the switchable magnetic field sensor 307, 308 is enabled, it senses changes in magnetic fields. The switchable magnetic field sensor 307, 308 may be specially designed and/or fabricated to sense a magnetic field change associated with a swipe in a magnetic card reader. For example, the dimensions and/or materials of the switchable magnetic field sensor 307, 308 may be chosen to be sensitive to the magnetic fields associated with the read heads of magnetic card readers. Each switchable magnetic field sensor 307, 308 has an output that corresponds to the change in magnetic field that it detects.

The logic unit 201 is electrically connected to the output of each switchable magnetic field sensor 307, 308 and determines if the output corresponds to a standard magnetic field change. The standard magnetic field change is a value, a range, a signal, a waveform, or the like that corresponds to the expected change in magnetic field caused by a swipe of the swipeable computer in a magnetic card reader. The standard magnetic field change may be determined by recording and combining the output of one or more of the switchable magnetic field sensors 307, 308 in one or more swipeable computers of the present invention resulting from swiping the swipeable computers in one or more standard card readers.

The standard magnetic field change is stored in a memory unit 203 in the swipeable computer. The logic unit 201 compares the switchable magnetic field sensor output to the standard magnetic field change through analog or digital means or a combination of the two. If the logic unit 201 determines that that the switchable magnetic field sensor output corresponds to the standard magnetic field change, then it is probable that a legitimate swipe of the swipeable computer in magnetic card reader is taking place. In that case, the logic unit 201 initiates a write sequence in which one or more of the dynamic magnetic emulators 303, 304 communicates data to the magnetic card reader.

The system described above conserves power by only enabling the switchable magnetic field sensors 307, 308, which have a relatively high power consumption, for a period of time after the logic unit 201 determines that the change in capacitance corresponds to that expected from a swipe in a magnetic card reader.

Figure 4:
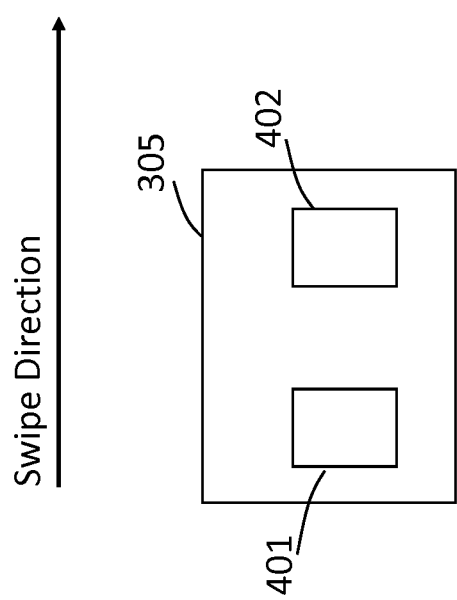
FIG. 4 illustrates an embodiment of a capacitive detector of the present invention.

FIG. 4 illustrates an embodiment of a capacitive detector 400 of the present invention. The capacitive detector 400 may comprise one or more capacitive sensors 401, 402. The output of the capacitive detector 400 may include one or both of the outputs of the capacitive sensors 401, 402 or a combination of the outputs. Using multiple capacitive sensors allows the swipeable computer to more-accurately detect a swipe in a magnetic card reader.

For example, the output of a single capacitive sensor resulting from a swipe through a magnetic card reader may be very similar to the output resulting from bringing the swipeable computer near the card reader or near anything made of materials similar to those of the card reader. But the combined outputs of capacitive sensors that are offset from each other in the swipe direction, like the capacitive sensors 401, 402 in FIG. 4, will differentiate a swipe from merely bringing the swipeable computer near a card reader or other similar materials.

In the example of FIG. 4, the capacitive sensor 402 will come close to the card reader first and will detect and output a corresponding change in capacitance. Thereafter, the capacitive sensor 401 will come close to the card reader and will detect and output a corresponding change in capacitance. But merely bringing the swipeable computer close to the card reader or other similar materials without the swiping motion will cause a simultaneous change in the capacitive sensors 401, 402 and/or a change in one not followed at the expected time by a change in the other. Thus, the combination of the outputs of the capacitive sensors 401, 402 can be compared to a standard capacitance change derived for the arrangement of the capacitive sensors 401, 402 for improved accuracy in swipe detection.

Figure 5:
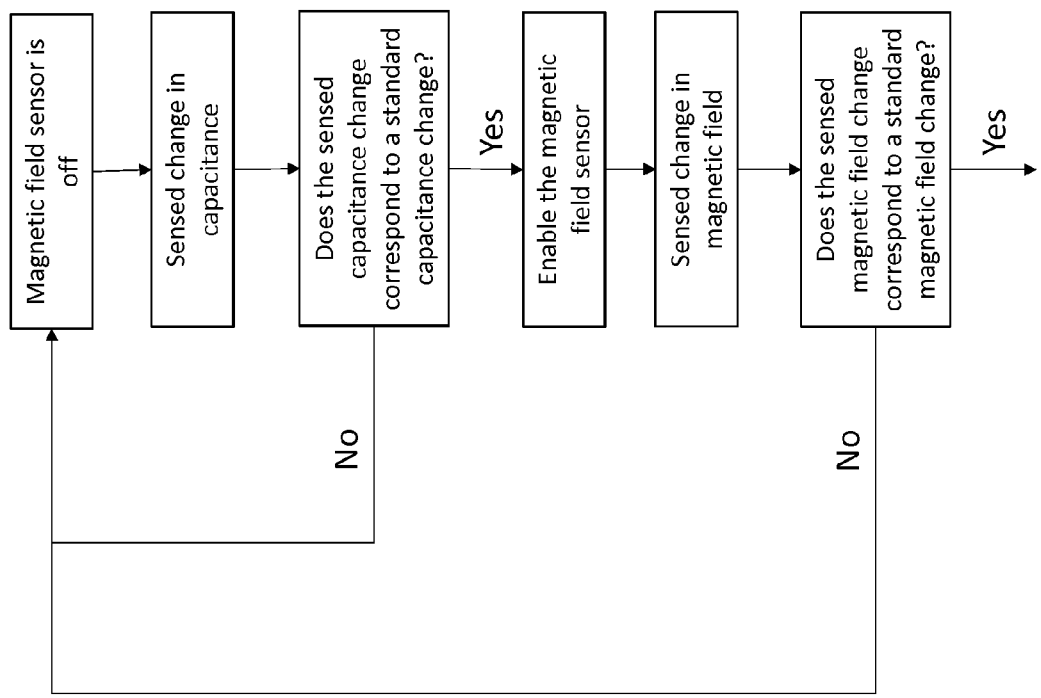
FIG. 5 illustrates an exemplary embodiment of a method for detecting a swipe of a swipeable computer in a magnetic card reader.

FIG. 5 illustrates an exemplary embodiment of a method for detecting a swipe of a swipeable computer in a magnetic card reader. As shown in FIG. 5, the method includes sensing a change in capacitance. Thereafter, the method includes determining if the change in capacitance corresponds to a standard capacitance change. If the change in capacitance does not correspond to a standard capacitance change, the magnetic field sensor remains off. The method also includes enabling a magnetic field sensor if the change in capacitance corresponds to the standard capacitance change. After the magnetic field sensor is enabled, the method includes sensing a magnetic field change. Detecting the magnetic field change may be accomplished using permanent magnets placed near the coil. The iron of the read head impinges on the static magnetic field of the permanent magnets. This impingement causes the static field to become dynamic, which induces a current in the coil which the device detects. Next, the method includes determining if the magnetic field change corresponds to a standard magnetic field change.

The step of sensing a change in capacitance of the above method may include sensing capacitive changes with a plurality of capacitive sensors. Additionally, the step of sensing a change in capacitance may include sensing capacitive changes with a plurality of capacitive sensors offset from each other in the swipe direction.

The devices and methods of the present invention may be used with a wide variety of magnetic card types. In one embodiment, the memory unit 203 of the swipeable computer is adapted to store user account information. User account information can include the information typically stored on the magnetic stripe of financial cards, gift cards, rewards cards, loyalty cards, hotel key cards, and the like.

In another embodiment, the display 102 of the swipeable computer shows the card type for the user account information. For example, if the swipeable computer has user account information for a Visa card stored thereon, the display 102 displays the Visa logo. Alternatively, if the swipeable computer has information corresponding to a Hilton hotel room key card stored thereon, the display 102 displays a Hilton logo.

The swipeable computer of the present invention may store user account information for a plurality of different accounts and/or cards. For example, the swipeable computer may store user account information for multiple credit cards and debit cards. In one embodiment, activating the button 103 of the swipeable computer toggles between the information for each of the plurality of financial cards and makes the information for one of the plurality of financial cards active. The active card is the one for which the magnetic emulator communicates information to the magnetic card reader when a swipe is detected. Further, the display 102 of the swipeable computer may show the card type for the active card.

In a further embodiment, the swipeable computer of the present invention is combined with a mobile communication device that contains an image of a card associated with the user account information. In this embodiment, if user account information for a Visa card is stored on the swipeable computer, the mobile communication device will contain an image of the Visa card. The combination of image with the swipeable computer may be important if a user is challenged by a merchant to prove that the user owns the original card. Also, the combination may be important if the user is required to know the card verification value (CVV) (also called the card security code (CSC), card verification data (CVD), card verification value code (CVVC), card verification code (CVC or CVC2), verification code (V-code or V code), card code verification (CCV), or signature panel code (SPC)) that is printed on the card.

One of ordinary skill in the art will appreciate that the techniques, structures and methods of the present invention above are exemplary. The present inventions can be implemented in various embodiments without deviating from the scope of the invention.

The invention claimed is:

1. A method for detecting a swipe of a swipeable computer in a magnetic card reader comprising:
providing the swipeable computer including:
a display;
a button;
a wireless communication unit;
a power source;
a dynamic magnetic emulator;
a capacitive detector having an output;
a switchable magnetic field sensor having an output;
a memory unit storing a standard capacitance change and a standard magnetic field change; and
a logic unit electrically connected to the capacitive detector output, the switchable magnetic field sensor, the switchable magnetic field sensor output, and the memory unit;
sensing with the capacitive detector a change in capacitance;
determining with the logic unit if the change in capacitance corresponds to the standard capacitance change;

enabling with the logic unit the magnetic field sensor if the change in capacitance corresponds to the standard capacitance change;
sensing with the switchable magnetic field sensor a magnetic field change; and
determining with the logic unit if the magnetic field change corresponds to the standard magnetic field change.

2. The method of claim 1, wherein the sensing a change in capacitance step comprises sensing capacitive changes with a plurality of capacitive sensors.

3. The method of claim 1, wherein the sensing a change in capacitance step comprises sensing capacitive changes with a plurality of capacitive sensors offset from each other in the swipe direction.

4. The method of claim 1, wherein the standard capacitance change is a change in capacitance associated with initiation of a swipe in a standard magnetic card reader.

5. The method of claim 1, wherein the standard magnetic field change is a change in magnetic field associated with initiation of a swipe in a standard magnetic card reader.

6. A method for detecting a swipe of a swipeable computer in a magnetic card reader comprising:
sensing a change in capacitance;
determining if the change in capacitance corresponds to a standard capacitance change;
enabling a magnetic field sensor if the change in capacitance corresponds to the standard capacitance change;
sensing a magnetic field change; and
determining if the magnetic field change corresponds to a standard magnetic field change.

7. The method of claim 6, wherein the sensing a change in capacitance step comprises sensing capacitive changes with a plurality of capacitive sensors.

8. The method of claim 6, wherein the sensing a change in capacitance step comprises sensing capacitive changes with a plurality of capacitive sensors offset from each other in the swipe direction.

9. The method of claim 6, wherein the standard capacitance change is a change in capacitance associated with initiation of a swipe in a standard magnetic card reader.

10. The method of claim 6, wherein the standard magnetic field change is a change in magnetic field associated with initiation of a swipe in a standard magnetic card reader.

11. A method for detecting a motion of a swipeable computer comprising:
sensing a change in capacitance;
determining if the change in capacitance corresponds to a standard capacitance change;
enabling a magnetic field sensor if the change in capacitance corresponds to the standard capacitance change;
sensing a magnetic field change; and
determining if the magnetic field change corresponds to a standard magnetic field change.

12. The method of claim 11, wherein the sensing a change in capacitance step comprises sensing capacitive changes with a plurality of capacitive sensors.

13. The method of claim 11, wherein the sensing a change in capacitance step comprises sensing capacitive changes with a plurality of capacitive sensors offset from each other in the swipe direction.

14. The method of claim 11, wherein the motion is a swipe in a magnetic card reader and the standard capacitance change is a change in capacitance associated with initiation of a swipe in a standard magnetic card reader.

15. The method of claim 11, wherein the motion is a swipe in a magnetic card reader and the standard magnetic field change is a change in magnetic field associated with initiation of a swipe in a standard magnetic card reader.

* * * * *